(12) United States Patent
Wang et al.

(10) Patent No.: US 9,062,039 B2
(45) Date of Patent: Jun. 23, 2015

(54) THERAPEUTIC COMPOUNDS

(71) Applicant: CHANGZHOU LE SUN PHARMACEUTICALS LIMITED, Jiangsu (CN)

(72) Inventors: Shudong Wang, Adelaide (AU); Hao Shao, Nottingham (GB)

(73) Assignee: CHANGZHOU LE SUN PHARMACEUTICALS LIMITED, Changzhou, Jiangsu (CN)

( * ) Notice: Subject to any disclaimer, the term of this patent is extended or adjusted under 35 U.S.C. 154(b) by 0 days.

(21) Appl. No.: 14/394,830

(22) PCT Filed: Apr. 18, 2013

(86) PCT No.: PCT/GB2013/050982
§ 371 (c)(1),
(2) Date: Oct. 16, 2014

(87) PCT Pub. No.: WO2013/156780
PCT Pub. Date: Oct. 24, 2013

(65) Prior Publication Data
US 2015/0105413 A1    Apr. 16, 2015

(30) Foreign Application Priority Data

Apr. 19, 2012    (GB) .................................. 1206908.4
Feb. 15, 2013    (GB) .................................. 1302704.0

(51) Int. Cl.
     *C07D 401/00*      (2006.01)
     *C07D 417/04*      (2006.01)

(52) U.S. Cl.
     CPC .................................. *C07D 417/04* (2013.01)

(58) Field of Classification Search
     USPC ........................................................ 544/331
     See application file for complete search history.

(56) References Cited

U.S. PATENT DOCUMENTS

2011/0195968 A1    8/2011    Greul et al.

FOREIGN PATENT DOCUMENTS

| GB | 2009118567 | * 10/2009 | ........... C07D 251/38 |
|----|------------|-----------|------------------------|
| WO | WO2007/033780 | 3/2007 | |
| WO | WO2009/118567 | 10/2009 | |

OTHER PUBLICATIONS

PCT Search Report and Written Opinion for PCT/GB2013/050982, completed May 16, 2013.
United Kingdom Search Report Under Section 17(5) for GB1206908.4, completed Jul. 31, 2012.
Shao, Hao, et al., "Substituted 4-(Thiazol-5-yl)-2-(phenylamino)pyrimidines Are Highly Active CDK9 Inhibitors: Synthesis, X-ray Crystal Structures, Structure-Activity Relationship, and Anticancer Activities", Feb. 14, 2013, Journal of Medicinal Chemistry, American Chemical Society, vol. 56, Nr:3, pp. 640-659.

* cited by examiner

*Primary Examiner* — Nizal Chandrakumar
(74) *Attorney, Agent, or Firm* — Barnes & Thornburg LLP (57) ABSTRACT

The present invention relates to compounds of formula (I): wherein $R_1$ is $NH_2$ or NHMe; $R_2$ is halo; and one of $R_3$ or $R_4$ is hydrogen and the other is selected from $-SO_2NH_2$, $-SO_2NHMe$ or $-SO_2NMe_2$, $-SO_2NHEt$, or $-SO_2NEt_2$; or a pharmaceutically acceptable salt or solvate thereof. The compounds of formula (I) are inhibitors of protein kinases, especially cyclic dependent kinases (CDKs) such as CDK9. The present invention also relates to processes for the preparation of these compounds, to pharmaceutical compositions comprising them, and to their use in the treatment of proliferative disorders, such as cancer, as well as other diseases or conditions in which protein kinase/CDK activity is implicated.

10 Claims, 3 Drawing Sheets

THERAPEUTIC COMPOUNDS

CROSS-REFERENCE TO RELATED APPLICATIONS

This application is a national stage entry under 35 USC §371(b) of PCT International Application No. PCT/GB2013/050982, filed Apr. 18, 2013, and claims the benefit of United Kingdom Patent Application No. 1206908.4, filed on Apr. 19, 2012, and United Kingdom Patent Application No. 1302704.0, filed on Feb. 15, 2013, all of which are expressly incorporated by reference herein.

INTRODUCTION

The present invention relates to therapeutic compounds. More specifically, the present invention relates to compounds that are inhibitors of protein kinase enzymes, especially cyclic dependent kinases (CDKs) such as CDK-9. The present invention also relates to processes for the preparation of these compounds, to pharmaceutical compositions comprising them, and to their use in the treatment of proliferative disorders, such as cancer, as well as other diseases or conditions in which protein kinase/CDK activity is implicated.

BACKGROUND OF THE INVENTION

Proliferative diseases, such as cancer, are characterised by uncontrolled and unregulated cellular proliferation. Precisely what causes a cell to proliferate in an uncontrolled and unregulated manner has been the focus of intense research over recent decades.

One important class of enzymes that has been the subject of extensive study in this regard is the protein kinase family. The protein kinase family is one of the largest in the human genome, comprising 500 genes. The majority of kinases contain a 250-300 amino acid residue catalytic domain with a conserved core structure. This domain comprises a binding pocket for ATP, whose terminal phosphate group transfers covalently to its macromolecular substrates. The protein kinases may be categorized by the substrates they phosphorylate, e.g. protein-serine/threonine, protein-tyrosine.

Protein kinases mediate intracellular signalling by effecting a phosphoryl transfer from a nucleoside triphosphate to a protein acceptor that is involved in a signalling pathway. These phosphorylation events are triggered in response to a variety of extracellular and other stimuli and act as molecular on/off switches that can modulate or regulate the target protein biological function. An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events. These diseases include, but are not limited to allergies and asthma, Alzheimer's disease, autoimmune diseases, bone diseases, cancer, cardiovascular diseases, inflammatory diseases, hormone-related diseases, metabolic diseases, neurological and neurodegenerative diseases. Accordingly, there has been a substantial effort in medicinal chemistry to find protein kinase inhibitors that are effective as therapeutic agents.

A wide variety of molecules capable of inhibiting protein kinase function through antagonising ATP binding are known in the art. In particular, it has been disclosed that 2-anilino-4-heteroaryl-pyrimidine compounds (Wang, S.; et al. WO 2003029248, Cyclacel Limited, UK. Fischer, P. M., WO2002079193, Cyclacel Limited, UK. Wang, S.; Fischer, P. M. US2002019404, Cyclacel Limited, UK.; Fischer, P. M.; Wang, S. WO2001072745, Cyclacel Limited, UK), and 2-anilino-4-phenyl-pyrimidine compounds (Wang S., et al. WO2005012262, Cyclacel Limited, UK) possess kinase inhibitory properties, particularly against cyclin-dependent kinases (CDKs).

Cyclin-dependent kinases (CDKs) are serine/threonine protein kinases that associate with various cyclin subunits, playing pivotal roles in the regulation of cell cycle progression and transcriptional cycle. Ten distinct CDKs (CDK1-9 and 11) are involved in a variety of important regulatory pathways in eukaryotic cells, including cell-cycle control, apoptosis, neuronal physiology, differentiation and transcription.

CDKs may be classified into two major groups, reflecting their functions. The cell cycle regulator CDKs composed primarily of CDK1, CDK2, CDK3, CDK4 and CDK6 function with their cyclin partners including cyclin A, B, D1, D2, D3, E, and F to regulate promotion of the cell cycle. The transcription regulator CDKs, which include CDK7, CDK8, CDK9 and CDK11 work together with cyclin C, H, K, L1, L2, T1 and T2, tend to play roles in transcriptional regulation.

The CDKs have been implicated in cell proliferation disorders, particularly in cancer. Cell proliferation is a result of the direct or indirect deregulation of the cell division cycle and the CDKs play a critical role in the regulation of the various phases of this cycle. Therefore, inhibitors of CDKs and their associated cyclins are useful targets for cancer therapy.

CDKs also play a role in apoptosis and T-cell development, which is predominantly due to the CDK functions in regulation of transcription. For example, clear clinical activity has very recently been obtained in chronic lymphocytic leukaemia (CLL) with CDK inhibitor flavopiridol. CLL is characterised by cellular resistance to apoptosis through up-regulation of anti-apoptotic proteins. Inhibition of transcription at the level of CDK9, which is necessary for mRNA elongation, selectively reinstates apoptosis in CLL cells. There is however a need for pharmacologically and pharmaceutically superior CDK inhibitors with a well-defined kinase selectivity and cellular specificity profile and anti-CLL efficacy, as well as efficacy against other CDK mediated disorders.

Furthermore, numerous viruses require CDKs, particular CDK2, CDK7, and CDK9, for their replication process. CDK inhibitors that restrain viral replication including human immunodeficiency virus, human cytomegalovirus, herpes virus, and varicella-zoster virus have been reported.

Inhibition of CDKs, in particular CDK9, is a novel strategy for potential treatment of cardiovascular diseases including cardiohypertrophy. Cardiohypertrophy is characterised by global increases in mRNA and protein synthesis. CDK7 and CDK9 are closely associated with cardiac hypertrophy as they are the main drivers for transcription. Therefore inhibition of CDK9 and its associated cyclins is a relevant drug target for cardiovascular diseases.

Inhibition of CDKs is also useful for the treatment of neurodegenerative disorders such as Alzheimer's disease. The appearance of Paired Helical Filaments, associated with Alzheimer's disease, is caused by the hyperphosphorylation of Tau protein by CDK5/p25.

International Patent Publication No. WO2009/118567 (Cancer Research Technology Limited) discloses a series of substituted-2-anilino-4-arylpyrimidines and substituted-4-aryl-[1,3,5]triazin-2-ylphenyl amines that possess broad therapeutic application as protein kinase inhibitors. The compounds described in WO2009/118567 are all potentially useful therapeutic agents for the treatment of diseases or conditions in which protein kinase hyperactivity (and, in particular, CDK hyperactivity) is implicated.

However, there remains a need to identify new therapeutic agents that can be used to treat such conditions. In particular there is a need to identify further compounds that function as inhibitors of protein kinase (and especially CDK) activity and which also possess one or more advantageous pharmaceutical properties. The one or more advantageous pharmaceutical properties may be selected from the group consisting of: increased potency/target activity (such as increased anti-proliferative activity); increased therapeutic efficacy (such as increased activity against certain cancer cell lines and/or improved selectivity for cancer cells); and/or improved bioavailability (such as oral bioavailability).

SUMMARY OF THE INVENTION

In one aspect, the present invention provides a compound, or a pharmaceutically acceptable salt or solvate thereof as defined herein.

In another aspect, the present invention provides a pharmaceutical composition comprising a compound of the invention as defined herein, or a pharmaceutically acceptable salt or solvate thereof, and one or more pharmaceutically acceptable excipients.

In another aspect, the present invention relates to a compound of the invention as defined herein, or a pharmaceutically acceptable salt or solvate thereof, or a pharmaceutical composition as defined herein, for use in therapy.

In another aspect, the present invention relates to a compound of the invention as defined herein, or a pharmaceutically acceptable salt or solvate thereof, or a pharmaceutical composition as defined herein, for use in the treatment of diseases or conditions in which protein kinase activity is implicated.

In another aspect, the present invention relates to the use of a compound of the invention as defined herein, or a pharmaceutically acceptable salt or solvate thereof, in the manufacture of a medicament for use in the treatment of diseases or conditions in which protein kinase activity is implicated.

In another aspect, the present invention relates to a method of treating a disease or condition in which protein kinase activity is implicated, said method comprising administering to a subject in need of such treatment a therapeutically effective amount of a compound of the invention as defined herein, or a pharmaceutically acceptable salt or solvate thereof, or a pharmaceutical composition as defined herein.

In another aspect, the present invention provides a compound, or a pharmaceutically acceptable salt or solvate thereof, or a pharmaceutical composition as defined herein, for use in the treatment of a proliferative disorder, such as cancer. In a particular embodiment, the cancer is a human cancer.

In another aspect, the present invention provides the use of a compound, or a pharmaceutically acceptable salt or solvate thereof, in the manufacture of a medicament for use in the treatment of a proliferative disorder, such as cancer. In a particular embodiment, the cancer is a human cancer.

In another aspect, the present invention provides a method of treating a proliferative disorder, such as cancer, said method comprising administering to a subject in need of such treatment a therapeutically effective amount of a compound, or a pharmaceutically acceptable salt or solvate thereof, or a pharmaceutical composition as defined herein. In a particular embodiment, the cancer is a human cancer.

In another aspect, the present invention provides a compound, or a pharmaceutically acceptable salt or solvate thereof, or a pharmaceutical composition as defined herein, for use in the production of a protein kinase inhibitory effect.

In another aspect, the present invention provides the use of a compound, or a pharmaceutically acceptable salt or solvate thereof, in the manufacture of a medicament for use in the production of a protein kinase inhibitory effect.

In another aspect, the present invention provides a method of producing a protein kinase inhibitory effect in vitro, said method comprising administering an effective amount of a compound, or a pharmaceutically acceptable salt or solvate thereof.

In another aspect, the present invention provides a method of producing a protein kinase inhibitory effect in vivo, said method comprising administering an effective amount of a compound, or a pharmaceutically acceptable salt or solvate thereof.

In another aspect, the present invention provides a compound, or a pharmaceutically acceptable salt or solvate thereof, or a pharmaceutical composition as defined herein, for use in the production of a CDK inhibitory effect.

In another aspect, the present invention provides the use of a compound, or a pharmaceutically acceptable salt or solvate thereof, in the manufacture of a medicament for use in the production of a CDK inhibitory effect.

In another aspect, the present invention provides a method of producing a CDK inhibitory effect in vitro, said method comprising administering an effective amount of a compound, or a pharmaceutically acceptable salt or solvate thereof.

In another aspect, the present invention provides a method of producing a CDK inhibitory effect in vivo, said method comprising administering an effective amount of a compound, or a pharmaceutically acceptable salt or solvate thereof In another aspect, the present invention provides a method of inhibiting CDKs in vitro or in vivo, said method comprising contacting a cell with an effective amount of a compound as defined herein, or a pharmaceutically acceptable salt or solvate thereof.

In another aspect, the present invention provides a method of inhibiting cell proliferation in vitro or in vivo, said method comprising contacting a cell with an effective amount of a compound as defined herein, or a pharmaceutically acceptable salt or solvate thereof.

The present invention further provides a method of synthesising a compound, or a pharmaceutically acceptable salt or solvate thereof, as defined herein.

In another aspect, the present invention provides a compound, or a pharmaceutically acceptable salt or solvate thereof, obtainable by, or obtained by, or directly obtained by a method of synthesis as defined herein.

In another aspect, the present invention provides novel intermediates as defined herein which are suitable for use in any one of the synthetic methods set out herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "halo" refers to fluoro, chloro, bromo and iodo.

The phrase "compound of the invention" means those compounds which are disclosed herein, both generically and specifically.

Compounds of the Invention

As previously stated, International Patent Publication No. WO2009/118567 (Cancer Research Technology Limited) discloses a series of substituted-2-anilino-4-arylpyrimidines and substituted-4-aryl-[1,3,5]triazin-2-ylphenyl amines that possess broad therapeutic application as protein kinase inhibitors.

One particular compound disclosed in WO2009/118567 is 3-(5-cyano-4-(4-methyl-2-(methylamino)thiazol-5-yl)pyrimidin-2-ylamino)benzenesulfonamide (compound 1.9 in WO2009/118567). The structure of the compound is shown below:

In a first aspect, the present invention provides a compound of formula I shown below:

wherein:
$R_1$ is $NH_2$ or NHMe;
$R_2$ is halo; and
one of $R_3$ or $R_4$ is hydrogen and the other is selected from —$SO_2NH_2$, —$SO_2NHMe$, —$SO_2NMe_2$, $SO_2NHEt$ or $SO_2NEt_2$;
or a pharmaceutically acceptable salt or solvate thereof.

The compounds of the present invention demonstrate one or more advantageous pharmaceutical properties relative to 3-(5-cyano-4-(4-methyl-2-(methylamino)thiazol-5-yl)pyrimidin-2-ylamino)benzenesulfonamide (compound 1.9 in WO2009/118567). In particular, the compounds of the present invention possess improved potency relative to this compound (which is demonstrated by increased activity in relation to certain specific enzyme targets and/or in terms of anti-proliferative activity in certain cell lines). Certain compounds of the invention also demonstrate improved oral bioavailability relative to this prior art compound.

Particular compounds of the invention include, for example, compounds of the formula I, or pharmaceutically acceptable salts thereof, wherein, unless otherwise stated, each of $R_1$, $R_2$, $R_3$ or $R_4$ has any of the meanings defined hereinbefore or in any of paragraphs (1) to (13) hereinafter:—

(1) $R_1$ is $NH_2$;
(2) $R_1$ is NHMe;
(3) $R_2$ is fluoro, chloro or bromo;
(4) $R_2$ is fluoro or chloro;
(5) $R_2$ is fluoro;
(6) one of $R_3$ or $R_4$ is hydrogen and the other is —$SO_2NH_2$, $SO_2NHMe$, or —$SO_2NMe_2$;
(7) one of $R_3$ or $R_4$ is hydrogen and the other is —$SO_2NH_2$;
(8) $R_4$ is hydrogen and $R_3$ is selected from —$SO_2NH_2$, —$SO_2NHMe$, or —$SO_2NMe_2$;
(9) $R_3$ is hydrogen and $R_4$ is selected from —$SO_2NH_2$, —$SO_2NHMe$ or —$SO_2NMe_2$;
(10) $R_3$ is hydrogen and $R_4$ is selected from —$SO_2NH_2$ or —$SO_2NHMe$;
(11) $R_3$ is hydrogen and $R_4$ is —$SO_2NH_2$;

Suitably, $R_2$ is fluoro or chloro, especially fluoro.

Suitably, one of $R_3$ or $R_4$ is hydrogen and the other is —$SO_2NH_2$. In a particular embodiment, $R_3$ is hydrogen and $R_4$ is —$SO_2NH_2$.

In a particular group of compounds of the invention, $R_1$ is —NHMe, i.e. the compounds have the structural formula Ia shown below:

wherein $R_2$, $R_3$ and $R_4$ have any one of the meanings defined herein, or a pharmaceutically acceptable salt or solvate thereof.

In a further group of compounds of the invention, $R_2$ is fluoro, i.e. the compounds have the structural formula Ib shown below:

wherein $R_1$, $R_3$ and $R_4$ have any one of the meanings defined herein, or a pharmaceutically acceptable salt or solvate thereof.

In a particular group of compounds of the invention, $R_1$ is —NHMe and $R_2$ is fluoro, i.e. the compounds have the structural formula Ic shown below:

wherein $R_3$ and $R_4$ have any one of the meanings defined herein, or a pharmaceutically acceptable salt or solvate thereof.

Particular compounds of the present invention include any one of the following:
3-(5-fluoro-4-(4-methyl-2-(methylamino)thiazol-5-yl)pyrimidin-2-ylamino)benzene sulfonamide;
3-(5-fluoro-4-(4-methyl-2-aminothiazol-5-yl)pyrimidin-2-ylamino)benzene sulfonamide;
3-(5-chloro-4-(4-methyl-2-(methylamino)thiazol-5-yl)pyrimidin-2-ylamino)benzene sulfonamide;
or a pharmaceutically acceptable salt or solvate thereof.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid.

The present invention also encompasses compounds of the invention as defined herein which comprise one or more isotopic substitutions. For example, H may be in any isotopic form, including $^1H$, $^2H(D)$, and $^3H$ (T); C may be in any isotopic form, including $^{12}C$, $^{13}C$, and $^{14}C$; and O may be in any isotopic form, including $^{16}O$ and $^{18}O$; and the like.

It is also to be understood that certain compounds of the invention may exist in solvated as well as unsolvated forms such as, for example, hydrated forms. It is to be understood that the invention encompasses all such solvated forms that possess protein kinase inhibitory activity.

It is also to be understood that certain compounds of the invention may exhibit polymorphism, and that the invention encompasses all such forms that possess protein kinase inhibitory activity.

Compounds of the invention containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, $4^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compounds of the invention may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable amide derivatives that may be formed at an amino group in a compound of the invention.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);

b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula I that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

It shall also be appreciated that compounds of formula I may also be covalently linked (at any suitable position) to other groups such as, for example, solubilising moieties (for example, PEG polymers), moieties that enable them to be bound to a solid support (such as, for example, biotin-containing moieties), and targeting ligands (such as antibodies or antibody fragments).

Synthesis

In the description of the synthetic methods described below and in the referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3.OEt_2$. A suitable alternative protecting group for a primary amino group is, for example, a phthaloyl group which may be removed by treatment with an alkylamine, for example dimethylaminopropylamine, or with hydrazine.

The compounds of the present invention may be prepared by using the general synthetic techniques described in WO2009/118567, the entire contents of which are incorporated herein by reference.

In a particular aspect, the present invention provides a method of synthesising a compound of the formula I, or a pharmaceutically acceptable salt or solvate thereof, the method comprising:

a) reacting a compound of formula A:

wherein $R_1$ and $R_2$ each have any one of the meanings set out hereinbefore;

with a compound of formula B:

wherein $R_3$ and $R_4$ have any one of the meanings set out hereinbefore; and b) optionally thereafter, and if necessary:
   i) removing any protecting groups present;
   ii) converting the compound formula I into another compound of formula I; and/or
   iii) forming a pharmaceutically acceptable salt or solvate thereof.

Suitably the coupling reaction between the compound of formula A and formula B may take place in the presence of a suitable solvent. Any suitable solvent or solvent mixture may be used for this reaction. A person skilled in the art will know how to select suitable solvents or solvent mixtures for use in these reactions. Examples of suitable solvent include alcohols, acetonitrile, halogenated solvents, etc.

A person skilled in the art will be able to select appropriate reaction conditions to use in order to facilitate this reaction. Suitably, the reaction is carried out in anhydrous conditions and in the presence of an inert atmosphere, such as argon or nitrogen. The reaction may also be carried out an elevated temperature, such as, for example, within the range of 80 to 180° C. or, more suitably 100 to 160° C., for a suitable time period of, for example, 20 minutes to 48 hours. Suitably, the reaction is carried out under microwave heating, for example, at about 140° C. for about 45 minutes.

The resultant compound of formula I can be isolated and purified using techniques well known in the art.

The process defined herein may further comprise the step of subjecting the compound of formula I to a salt exchange, particularly in situations where the compound of formula I is formed as a mixture of different salt forms. The salt exchange suitably comprises immobilising the compound of formula I on a suitable solid support or resin, and eluting the compounds with an appropriate acid to yield a single salt of the compound of formula I.

Compounds of formula A can be prepared by processes known in the art. Examples of suitable procedures for the preparation of the compound of Formula A are shown in Scheme 1 below.

Scheme 1 a 3-Chloropentane-2,4-dione, pyridine, EtOH, r.t. 4 h;
b NCS or NBS or $Br_2$ in HBr, 1-3 h;
c 1,1-dimethoxy-N,N-dimethylmethanamine microwave, 140° C., 30-40 min;
d Selectfluor® MeCN, 0-5° C., 1 h.

Compounds of formula B can also be prepared by processes known in the art.

Pharmaceutical Compositions

According to a further aspect of the invention there is provided a pharmaceutical composition which comprises a compound of the invention as defined hereinbefore, or a pharmaceutically acceptable salt or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of proliferative disease is an amount sufficient to symptomatically relieve in a warm-blooded animal, particularly a human the symptoms of infection, to slow the progression of infection, or to reduce in patients with symptoms of infection the risk of getting worse.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The compounds of the invention are inhibitors of protein kinase activity.

Thus, in another aspect, the present invention provides a method of inhibiting protein kinase activity in a cell, the method comprising administering to said cell compound of formula I as defined herein, or a pharmaceutically acceptable salt or solvate thereof.

In a further aspect, the present invention provides a method of inhibiting protein kinase in vitro or in vivo, said method comprising contacting a cell with an effective amount of a compound, or a pharmaceutically acceptable salt or solvate thereof, as defined herein.

In another aspect, the present invention provides a method of inhibiting protein kinase activity in a human or animal subject in need of such inhibition, the method comprising administering to said subject an effective amount of a compound of formula I as defined herein, or a pharmaceutically acceptable salt or solvate thereof.

Suitably, the protein kinase is selected from one or more of the following group: CDKs, aurora kinase, GSK, and/or Tyrosine kinases.

The compounds of the present invention demonstrate particular inhibitory activity against CDK9T1, CDK1B, CDK2A, CDK5p35, CDK6D3, CDK7H, Aurora A, Aurora B, and GSK3B.

The compounds of the present invention are suitable for the treatment of any diseases or conditions in which one or more of the protein kinase targets outlined above are implicated.

In one embodiment, the compounds are suitable for inhibition of a proliferative disorder mediated by one of the aforementioned protein kinase targets.

The term "proliferative disorder" is used herein in a broad sense to include any disorder that requires control of the cell cycle, for example cancers and other disorders associated with uncontrolled cellular proliferation such as dermatological disorders such as psoriasis, certain viral disorders, certain cardiovascular diseases such as restenosis and cardiomyopathy, certain CNS disorders, auto-immune disorders such as glomerulonephritis and rheumatoid arthritis, hormone-related diseases, metabolic disorders, stroke, alopecia, emphysema, inflammatory diseases, or infectious diseases such fungal diseases or parasitic disorders such as malaria. In these disorders, the compounds of the present invention may induce apoptosis or maintain stasis within the desired cells as required.

Preferably the compound of formula I is capable of inhibiting one or more of the host cell kinases involved in cell proliferation, viral replication, cardiovascular disorders, neurodegeneration, autoimmunity, a metabolic disorder, stroke, alopecia, an inflammatory disease or an infectious disease.

In an embodiment, the proliferative disorder is cancer. The cancer may be selected from the group consisting of chronic lymphocytic leukaemia (CLL), lymphoma, leukaemia, breast cancer, lung cancer, prostate cancer, colon cancer, melanoma, pancreatic cancer, ovarian cancer, squamous carcinoma, carcinoma of head and neck, endometrial cancer, and oesophageal carcinoma.

Preferably, the proliferative disorder is a cancer, such as a leukaemia.

In a particular embodiment, the compounds of the invention are useful for the treatment of leukaemia, especially chronic lymphoid leukaemia (CLL).

As defined herein an effect against a proliferative disorder mediated by a kinase within the scope of the present invention may be demonstrated by the ability to inhibit cell proliferation in an in vitro whole cell assay, for example using any of the cell lines including, but not limiting to, A549, A2780, HT29, Saos-2, HCT-116, HeLa, MCF-7, NCI-H460 or by showing inhibition of a CDK enzyme such as CDK1, CDK2, CDK4, CDK5, CDK6, CDK7, CDK8, CDK9, CDK11, or other protein kinases in an appropriate assay. These assays including methods for their performance are described in more detail in the accompany examples. A further embodiment relates to the use of compounds of the invention, or pharmaceutically acceptable salts thereof, in the manufacture of a medicament capable of treating a viral disorder mediated by one or more of the host cell CDKs involved in viral replication, i.e. CDK1, CDK2, CDK4, CDK7, CDK8, CDK9 or CDK11 as hereinbefore defined. Preferably such medicament is useful in treating a viral disorder.

Assays for determining CDK activity are described in more detail in the accompanying examples. Using such enzymes assays it may be determined whether a compound is anti-viral in the context of the present invention.

Preferably such medicament is useful in the treatment of viral disorders, such as human cytomegalovirus (HCMV), herpes simplex virus type 1 (HSV-1), human immunodeficiency virus type 1 (HIV-1), and varicella zoster virus (VZV).

Typically such disorder is CDK dependent or sensitive. CDK dependent disorders are associated with an above normal level of activity of one or more CDK enzymes. Such disorders are typically associated with an abnormal level of activity of CDK1, CDK2, CDK4, CDK7, CDK8, CDK9 and/or CDK11. A CDK sensitive disorder is a disorder in which an aberration in the CDK level is not the primary cause, but is downstream of the primary metabolic aberration. In such scenarios, CDK1, CDK2, CDK4, CDK7, CDK8 CDK9 and/or CDK11 can be said to be part of the sensitive metabolic pathway and inhibitors of these CDKs may therefore be active in treating such disorders.

For use in the treatment of viral disorders, preferably the medicament of the invention is capable of inhibiting CDK2, CDK7, and/or CDK9.

Yet another embodiment relates to the use of compounds of the invention, or pharmaceutically acceptable salts thereof, in the manufacture of a medicament capable of treating cardiovascular diseases mediated by one or more CDKs. Preferably such medicament is useful in treating cardiovascular diseases.

A cardiovascular disease may be selected from the group consisting of ischaemic heart disease (also known as myocardial infarction or angina), hypertension, heart failure, restenosis and cardiomyopathy.

Cardiac hypertrophy is characterised by global increases in mRNA and protein synthesis. CDK9 activity has been demonstrated to be necessary for hypertrophy in cardiomyocytes. Heart-specific activation of CDK9 by cyclin T1 was found to provoke hypertrophy. Compounds of the invention are believed to inhibit CDK9 and are therefore believed to be of use in the prevention and treatment of cardiac hypertrophy.

Yet another embodiment relates to the use of a compound of the invention in the manufacture of a medicament capable of treating neurodegenerative disorders mediated by one or more GSKs or CDKs. Preferably such medicament is useful in the treatment of neurodegenerative disorders such as Alzheimer's disease.

Tau is a GSK-3 substrate which has been implicated in the etiology of Alzheimer's disease. In healthy nerve cells, Tau co-assembles with tubulin into microtubules. However, in Alzheimer's disease, tau forms large tangles of filaments, which disrupt the microtubule structures in the nerve cell, thereby impairing the transport of nutrients as well as the transmission of neuronal messages. It is believed that GSK3 inhibitors may be able to prevent and/or reverse the abnormal hyperphosphorylation of the microtubule-associated protein tau that is an invariant feature of Alzheimer's disease and a number of other neurodegenerative diseases, such as progressive supranuclear palsy, corticobasal degeneration and Pick's disease. Mutations in the tau gene cause inherited forms of fronto-temporal dementia, further underscoring the relevance of tau protein dysfunction for the neurodegenerative process.

The appearances of Paired Helical Filaments, associated with Alzheimer's disease, are caused by the hyperphosphorylation of Tau protein by CDK5-p25. Compounds of the invention are believed to inhibit CDK5 and are therefore believed to be of use in the prevention and treatment of neurodegenerative disorders.

Another embodiment relates to the use of compounds of the invention, or pharmaceutically acceptable salts thereof, in the manufacture of a medicament for treating a metabolic disorder mediated by one or more GSKs. Preferably the medicament is useful in treating metabolic disorders.

Metabolic disorders include Type II diabetes (non insulin dependent diabetes mellitus) and diabetic neuropathy. Compounds of the invention are believed to inhibit GSK-3, which is implicated in Type II diabetes.

GSK3 is one of several protein kinases that phosphorylate glycogen synthase (GS) and is involved in the stimulation of glycogen synthesis by insulin in skeletal muscle. GSK3's action on GS thus results in the latter's deactivation and thus suppression of the conversion of glucose into glycogen in muscles. Type II diabetes (non-insulin dependent diabetes mellitus) is a multi-factorial disease. Hyperglycaemia is due to insulin resistance in the liver, muscles, and other tissues, coupled with impaired secretion of insulin. Skeletal muscle is the main site for insulin-stimulated glucose uptake, there it is either removed from circulation or converted to glycogen. Muscle glycogen deposition is the main determinant in glucose homeostasis and type II diabetics have defective muscle glycogen storage. There is evidence that an increase in GSK3 activity is important in type II diabetes.

Another embodiment relates to the use of compounds of the invention, or pharmaceutically acceptable salts thereof, in the manufacture of a medicament for treating bipolar disorder mediated by one or more kinases. Preferably such medicament is useful in treating bipolar disorder.

Yet another embodiment relates to the use of compounds of the invention, or pharmaceutically acceptable salts thereof, in the manufacture of a medicament for treating a stroke mediated by one or more GSKs. Preferably such medicament is useful in treating a stroke.

Reducing neuronal apoptosis is an important therapeutic goal in the context of head trauma, stroke, epilepsy, and motor neuron disease. GSK3 as a pro-apoptotic factor in neuronal cells makes this protein kinase an attractive therapeutic target for the design of inhibitory drugs to treat these diseases.

Yet another embodiment relates to the use of compounds of the invention, or pharmaceutically acceptable salts thereof, in the manufacture of a medicament for treating alopecia mediated by one or more GSKs. Preferably such medicament is useful in treating alopecia.

The ectopic application of GSK3 inhibitors may be therapeutically useful in the treatment of baldness and in restoring hair growth following chemotherapy-induced alopecia.

A further aspect of the invention relates to a method of treating a condition mediated by one or more enzymes selected from a CDK, aurora kinase, GSK, or tyrosine kinase enzyme as hereinbefore defined.

In one preferred embodiment such condition is a GSK3-dependent disorder, said method comprising administering to a subject in need thereof, a compound of the invention or a pharmaceutically acceptable salt or solvate thereof, as defined above in an amount sufficient to inhibit GSK3.

Preferably, the compound of the invention, or pharmaceutically acceptable salt or solvate thereof, is administered in an amount sufficient to inhibit GSK3β.

In another preferred embodiment, the invention relates to a method of treating an aurora kinase-dependent disorder, said method comprising administering to a subject in need thereof, a compound of the invention or a pharmaceutically acceptable salt or solvate thereof, as defined above in an amount sufficient to inhibit an aurora kinase.

Preferably the compound of the invention is administered in an amount sufficient to inhibit aurora kinase A, aurora kinase B or aurora kinase C.

In another preferred embodiment, the invention relates to a method of treating a tyrosine kinase-dependent disorder, said method comprising administering to a subject in need thereof, a compound of the invention or a pharmaceutically acceptable salt or solvate thereof, as defined above in an amount sufficient to inhibit a tyrosine kinase.

In another preferred embodiment, the invention relates to a method of selectively treating a protein kinase-dependent disorder, said method comprising administering to a subject in need thereof, a compound of the invention or a pharmaceutically acceptable salt or solvate thereof, as defined above in an amount sufficient to inhibit a selected protein kinase. Preferably said method comprising contacting said protein kinase with a compound of the invention.

Preferably the compound of the invention is administered in an amount sufficient to inhibit at least one protein kinase, such as CDK, GSK, aurora kinase, BCR-ABL, IKK, FLT3, or MNKs or another tyrosine kinase.

In a preferred embodiment of this aspect, the protein kinase is a CDK. Preferably, the protein kinase is CDK1, CDK2, CDK3, CDK4, CDK5, CDK6, CDK7, CDK8, CDK9 and CDK11, more preferably CDK1, CDK2, CDK5 or CDK9.

Known CDK inhibitors under development suffer from a number of problems including a promiscuous kinase inhibitor profile which, apart from multiple CDK inhibition, also potently inhibits other kinases, resulting in observations of toxicity. Other CDK inhibitors under clinical and late-clinical predevelopment are either pan-specific, belonging to the oligo-specific CDK2-CDK7-CDK9 class or are CDK4/6 specific. Although discovery-stage compounds with modest CDK9 selectivity (>10 fold with respect to CDK2 and/or CDK7) have been reported, the determinants for CDK9 selectivity are not currently understood in the published art.

In a particular embodiment, the compounds of the invention are useful for the treatment of leukaemia, especially chronic lymphoid leukaemia (CLL).

Our research derives from the consideration that apoptotic ability in CLL and other tumour cells can be reinstated by interference with the expression of anti-apoptotic proteins at the transcriptional level via RNAPII, and should provide a therapeutic margin for the elimination of CLL cells while sparing non-transformed quiescent and proliferative cells. Although other CDKs—including CDK1, CDK2, CDK8 and CDK11—have been implicated in the regulation of transcription, the roles of CDK7 and CDK9 appear to be most important in this respect. An important difference between CDK7 and CDK9 is the fact that CDK7 has an additional role as a general CDK-activating kinase (CAK), while CDK9 appears to function exclusively in the regulation of transcription. Apart from regulating transcriptional initiation and elongation, CDK9 also has functions in pre-mRNA splicing.

Results to date strongly suggest that inhibition of CDK9 is necessary and sufficient for effective reversal of apoptotic resistance in CLL. Of all the CDKs involved in RNAPII C-terminal domain (CTD) phosphorylation, CDK9 is unique in apparently lacking cell-cycle related roles. However studies on the effect of depletion of CDK1, CDK2, CDK7 and CDK9 on cellular apoptosis suggest that inhibition of cell cycle CDK functions may not contribute to the elimination of CLL cells and may in fact be undesirable because of antiproliferative effects on nontransformed cells in general, which may manifest as toxicity.

Our research has enabled us to distinguish, both phenotypically and biochemically, between compounds that inhibit RNAP-II CDKs and those that act predominantly through inhibition of cell cycle CDKs (CDK1, CDK2, CDK4, CDK6) or the closely related mitotic kinases.

In one embodiment of the invention the compound of formula I is capable of inhibiting at least one CDK enzyme, preferably at least one of CDK1, CDK2, CDK5 and CDK9.

In a further preferred embodiment compounds of formula I are capable of exhibiting an antiproliferative effect in human cell lines, as measured by a standard 72 h MTT cytotoxicity assay. Preferably the compound of formula I exhibits an $IC_{50}$ value of less than 1 micromolar.

In a further aspect of the invention there is provided a method of treating a proliferative disease or disorder, a viral disorder, a cardiovascular disease, a CNS disorder, an autoimmune disease, a metabolic disorder, stroke, alopecia, an inflammatory disease or an infectious disease, said method comprising administering to a subject in need thereof, a compound of formula I as hereinbefore defined in an effective amount.

The use of a compound of the invention in the manufacture of a medicament as hereinbefore defined includes the use of the compound directly, or in any stage of the manufacture of such a medicament, or in vitro in a screening programme to identify further agents for the prevention or treatment of the hereinbefore defined diseases or conditions.

A further aspect of the invention relates to the use of a compound of formula I or a pharmaceutically acceptable salt or solvate or physiologically hydrolysable, solubilising or immobilising derivative thereof, in an assay for identifying candidate compounds capable of treating one or more disorders or diseases as hereinbefore defined. Preferably a compound is of use in identifying candidate compounds capable of inhibiting a protein kinase, more preferably one or more of a CDK, aurora kinase, GSK, or other tyrosine kinase enzyme.

In one aspect, the present invention provides a compound of Formula I, or a pharmaceutically acceptable salt or solvate thereof, or a pharmaceutical composition as defined herein for use in therapy.

In another aspect, the present invention provides a compound of formula I as defined herein, or a pharmaceutically acceptable salt or solvate thereof for use in the treatment of disease or condition associated with protein kinase activity.

In another aspect, the present invention provides the use of a compound of formula I as defined herein, or a pharmaceutically acceptable salt or solvate thereof, in the manufacture of a medicament for use in the treatment of disease or condition associated with protein kinase activity.

In yet another aspect, the present invention provides a method of treating a proliferative disorder in a human or animal subject, the method comprising administering to said subject a therapeutically acceptable amount of a compound of formula I as defined herein, or a pharmaceutically acceptable salt or solvate thereof.

In yet another aspect, the present invention provides a compound of formula I as defined herein, or a pharmaceutically acceptable salt or solvate thereof, for use in the treatment of a proliferative disorder.

In yet another aspect, the present invention provides the use of a compound of formula I as defined herein, or a pharmaceutically acceptable salt or solvate thereof, in the manufacture of a medicament for use in the treatment of a proliferative disorder.

In another aspect, the present invention provides a compound, or a pharmaceutically acceptable salt or solvate thereof, or a pharmaceutical composition as defined herein for use in the treatment of cancer.

In yet another aspect, the present invention provides the use of a compound, or a pharmaceutically acceptable salt or solvate thereof, as defined herein in the manufacture of a medicament for use in the treatment of cancer.

In yet another aspect, the present invention provides a method of treating cancer in a patient in need of such treatment, said method comprising administering to said patient a therapeutically effective amount of a compound, or a pharmaceutically acceptable salt or solvate thereof, or a pharmaceutical composition as defined herein.

The invention further provides a method of treatment of the human or animal body, the method comprising administering to a subject in need of treatment a therapeutically-effective amount of an active compound, preferably in the form of a pharmaceutical composition.

Routes of Administration

The compounds of the invention or pharmaceutical composition comprising the active compound may be administered to a subject by any convenient route of administration, whether systemically/peripherally or topically (i.e. at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The compounds of the invention may be administered alone as a monotherapy or may administered in combination with one or more additional therapeutic agents. The selection of the one ore more additional therapeutic agents will of course vary depending on the disease or condition to be treated and its severity.

It is commonplace to use combination therapies to treat proliferative disorders, such as cancer. Therefore, the antiproliferative treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, melphalan, chlorambucil, busulphan, temozolomide and nitrosoureas); antimetabolites (for example gemcitabine and antifolates such as fluoropyrimidines like 5-fluorouracil and tegafur, raltitrexed, methotrexate, cytosine arabinoside, fludarabine and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint/combination treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to a particular aspect of the invention there is provided a combination suitable for use in the treatment of a disease or condition in which protein kinase activity is implicated as defined herein (e.g. cancer), comprising a compound of the invention as defined hereinbefore, or a pharmaceutically acceptable salt or solvate thereof, and another therapeutic agent (e.g. an anti-tumour agent).

According to this aspect of the invention there is provided a combination suitable for use in the treatment of a cancer (for example a cancer involving a solid tumour) comprising a compound of the invention as defined hereinbefore, or a pharmaceutically acceptable salt or solvate thereof, and any one of the anti-tumour agents listed under (i)-(ix) above.

In a further aspect of the invention there is provided a compound of the invention or a pharmaceutically acceptable salt or solvate thereof, in combination with an anti-tumour agent selected from one listed under (i)-(ix) herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt or solvate thereof in combination with one or more additional therapeutic agents (for example, an anti-tumour agent selected from one listed under (i)-(ix) herein above), in association with a pharmaceutically acceptable diluent or carrier.

According to a particular aspect of the invention there is provided a combination suitable for use in the treatment of cancer, in particular a leukaemia such as chronic lymphocytic leukaemia (CLL), comprising a compound of the invention as defined hereinbefore, or a pharmaceutically acceptable salt or solvate thereof, and another therapeutic agent (e.g. an anti-tumour agent).

According to this aspect of the invention there is provided a combination suitable for use in the treatment of a cancer, in particular a leukaemia such as CLL, comprising a compound of the invention as defined hereinbefore, or a pharmaceutically acceptable salt or solvate thereof, and any one of the anti-tumour agents listed under (i)-(ix) above.

In a further aspect of the invention there is provided a compound of the invention or a pharmaceutically acceptable salt or solvate thereof, for use in the treatment of cancer, in particular a leukaemia such as CLL, in combination with an anti-tumour agent selected from one listed under (i)-(ix) herein above.

According to a further aspect of the invention there is provided a combination suitable for use in the treatment of cancer, in particular a leukaemia such as CLL, comprising a compound of the invention as defined hereinbefore, or a pharmaceutically acceptable salt or solvate thereof, and fludarabine, or a pharmaceutically acceptable salt or solvate thereof.

According to this aspect of the invention there is provided a combination suitable for use in the treatment of a cancer, in particular a leukaemia such as CLL, comprising a compound of the invention as defined hereinbefore, or a pharmaceutically acceptable salt or solvate thereof, and fludarabine, or a pharmaceutically acceptable salt or solvate thereof.

In a further aspect of the invention there is provided a compound of the invention or a pharmaceutically acceptable salt or solvate thereof, for use in the treatment of cancer, in particular a leukaemia such as CLL, in combination with fludarabine, or a pharmaceutically acceptable salt or solvate thereof.

EXAMPLES

Synthesis of Compounds

General $^1$H-NMR and $^{13}$C-NMR spectra were obtained using a Bruker 400 Ultrashield™ spectrometer at 400 MHz and 100 MHz respectively. These were analysed using the Bruker TOPSPIN 2.1 programme. Chemical shifts are reported in parts per million relative to internal tetramethylsilane standard. Coupling constants (J) are quoted to the nearest 0.1 Hz. The following abbreviations are used: s, singlet; d, doublet; t, triplet; q, quartet; qu, quintuplet; m, multiplet and br, broad. High resolution mass spectra were obtained using a Waters 2795 single quadrupole mass spectrometer/micromass LCT platform. TLC (thin-layer chromatography) was performed using alumina plates coated with silica gel G60. Developed plates were air dried and analysed under a UV lamp (254/365 nm). Silica gel (EM Kieselgel 60, 0.040-0.063 mm, Merck) or ISOLUTE pre-packed columns was used for flash chromatography. Melting points (mp) were determined with an Electrothermal melting point apparatus and are uncorrected.

Example 1

Preparation of 3-(5-Fluoro-4-(4-methyl-2-(methylamino)thiazol-5-yl)pyrimidin-2-ylamino)benzene sulfonamide (CDKI-73)

To a well-stirred solution of (Z)-3-(Dimethylamino)-1-(4-methyl-2-(methylamino)thiazol-5-yl)prop-2-en-1-one (which can be prepared using the method described previously in S. Wang et al. J Med Chem. 2004, 47, 1662-1675) (5 mmol) in MeOH under ice bath, Selecfluor® (5 mmol) was added and the reaction was continued for 1 hour. After completion of the reaction, the mixture was concentrated and purified by column chromatography using EtOAc to yield (Z)-3-(dimethylamino)-2-fluoro-1-(4-methyl-2-(methylamino)thiazol-5-yl)prop-2-en-1-one. Yellow solid (30%). $^1$H-NMR (DMSO-$d_6$) δ: 2.40 (s, 3H, $CH_3$), 2.83 (d, 3H, J=4.8 Hz, $CH_3$), 3.04 (d, 6H, J=1.6 Hz, 2×$CH_3$), 6.88 (d, 1H, J=30.4 Hz, CH), 8.04 (d, 1H, J=4.4 Hz, NH). HR-MS (m/z): calcd for $C_{10}H_{14}FN_3OS$, 243.0842; found 244.0849 [M+H]$^+$.

A mixture of (Z)-3-(dimethylamino)-2-fluoro-1-(4-methyl-2-(methylamino)thiazol-5-yl)prop-2-en-1-one (1 mmol) and 3-guanidinobenzenesulfonamide (2 mmol) in 2.5 mL 2-methoxyethanol was heated at 140° C. for 45 minutes under microwave radiation. The mixture was purified by column chromatography using EtOAc/PE or EtOAc/MeOH to yield the titled compound as yellow solid.

mp 268-270° C. Anal. RP-HPLC: $t_R$ 11.45 min, purity 99%. $^1$H-NMR (DMSO-$d_6$): δ 2.48 (s, 3H, $CH_3$), 2.88 (d, 3H, J=4.8 Hz, $CH_3$), 7.29 (s, 2H, $NH_2$), 7.40 (d, 1H, J=8.0 Hz, Ph-H), 7.47 (t, 1H, J=8.0 Hz, Ph-H), 7.89 (d, 1H, J=8.0 Hz, Ph-H), 8.13 (br q, 1H, J=4.8 Hz, NH), 8.25 (s, 1H, Ph-H), 8.47 (d, 1H, J=3.2 Hz, Py-H), 9.83 (s, 1H, NH). $^{13}$C-NMR (DMSO-$d_6$): δ 19.43 (d, J=5 Hz), 31.33, 109.97 (d, J=8 Hz), 115.81, 118.78, 121.89, 129.51, 141.46, 144.94, 145.97 (d, J=25 Hz), 147.63 (d, J=12 Hz), 147.94 (d, J=248 Hz), 155.66, 156.04, 171.34. HR-MS (ESI$^+$): m/z [M+H]$^+$ calcd for $C_{15}H_{16}FN_6O_2S_2$, 395.0760, found 395.0641.

Example 2

Preparation of 3-(4-(2-Amino-4-methylthiazol-5-yl)-5-fluoropyrimidin-2-ylamino)benzene sulfonamide To a solution of N'-(5-(3-(dimethylamino)acryloyl)-4-methylthiazol-2-yl)-N,N-dimethylformimid amide (S. Wang et al. J Med Chem. 2004, 47, 1662-1675) (5 mmol) in MeOH under ice bath, Selectfluor® (5 mmol) was added and the reaction was continued for 60 minutes. After completion of the reaction, the mixture was concentrated and purified by column chromatography using EtOAc to yield (5-((Z)-3-(dimethylamino)-2-fluoroacryloyl)-4-methylthiazol-2-yl)-N,N-dimethylformimidamide. Yellow solid (22%). $^1$H-NMR (DMSO-$d_6$) δ: 2.41 (s, 3H, $CH_3$), 2.98 (s, 3H, $CH_3$), 3.06 (d, 6H, J=1.6 Hz, 2×$CH_3$), 3.18 (s, 3H, $CH_3$), 6.95 (d, 1H, J=29.6 Hz, CH), 8.38 (s, 1H, NH). HR-MS (m/z): calcd for $C_{12}H_{17}FN_4OS$, 284.1107; found 285.1206 [M+H]$^+$.

A mixture of (5-((Z)-3-(dimethylamino)-2-fluoroacryloyl)-4-methylthiazol-2-yl)-N,N-dimethylformimidamide (1 mmol) and 3-guanidinobenzenesulfonamide (2 mmol) in 2.5 mL 2-methoxyethanol was heated at 140° C. for 45 minutes under microwave radiation. The mixture was purified by column chromatography using EtOAc/PE or EtOAc/MeOH to yield the titled compound as yellow solid. $^1$H-NMR (DMSO-$d_6$) δ: 2.48 (d, 3H, J=1.6 Hz, $CH_3$), 7.30 (s, 2H, $NH_2$), 7.40 (d, 1H, J=7.6 Hz, Ph-H), 7.47 (t, 1H, J=8.0 Hz, Ph-H), 7.60 (s, 2H, $NH_2$), 7.93 (d, 1H, J=8.4 Hz, Ph-H), 8.19 (s, 1H, Ph-H), 8.46 (d, 1H, J=3.6 Hz, Py-H), 9.81 (s, 1H, NH). HR-MS (m/z): calcd for $C_{14}H_{13}FN_6O_2S_2$, 380.0525; found 381.0475 [M+H]$^+$.

Example 3

Preparation of 3-(5-chloro-4-(4-methyl-2-(methylamino)thiazol-5-yl)pyrimidin-2-ylamino)benzene sulfonamide To a well stirred solution of (E)-3-(dimethylamino)-1-(4-methyl-2-(methylamino)thiazol-5-yl) prop-2-en-1-one (2 mmol) in 50 ml methanol N-chlorosuccinimide (2.5 mmol) was added. The reaction mixture was stirred for 30 minutes. The mixture was evaporated to dryness and the residue was purified by column chromatography using EtoAc to yield (Z)-2-chloro-3-(dimethylamino)-1-(4-methyl-2-(methylamino)thiazol-5-yl)prop-2-en-1-one as light yellow solid (43%). $^1$H-NMR (DMSO-$d_6$) δ: 2.37 (s, 3H, $CH_3$), 2.98 (s, 3H, $CH_3$), 3.25 (s, 6H, 2×$CH_3$), 6.43 (s, 1H, NH), 7.42 (s, 1H, CH). HR-MS (m/z): calcd for $C_{10}H_{14}ClN_3OS$, 259.0546; found 260.0541 [M+H]$^+$.

A mixture of above compound (1 mmol) and 3-guanidinobenzenesulfonamide (2 mmol) in 2.5 mL 2-methoxyethanol was heated at 140° C. for 30 minutes under microwave radiation. The mixture was purified by column chromatography using EtOAc to yield 3-(5-chloro-4-(4-methyl-2-(methylamino)thiazol-5-yl)pyrimidin-2-ylamino)benzene sulfonamide as yellow solid. $^1$H-NMR (MeOH-$d_6$) δ: 2.44 (s, 3H, $CH_3$), 2.99 (s, 3H, $CH_3$), 7.46 (t, 1H, J=8.0 Hz, Ph-H), 7.54 (m, 1H, Ph-H), 7.84 (m, 1H, Ph-H), 8.41 (t, 1H, J=1.2 Hz, Ph-H), 8.42 (s, 1H, Py-H). HR-MS (m/z): calcd for $C_{15}H_{16}ClN_6O_2S_2$, 410.0386; found 411.0530 [M+H]$^+$.

Comparative Example

Preparation of 3-(5-cyano-4-(4-methyl-2-(methylamino)thiazol-5-yl)pyrimidin-2-ylamino)benzenesulfonamide (comparator)

3-(5-cyano-4-(4-methyl-2-(methylamino)thiazol-5-yl)pyrimidin-2-ylamino)benzenesulfonamide was prepared as described in International Patent Publication No. WO2009/118567 (compound 1.9) and was used as a comparator in the biological section below.

Example 5

Biological Activity

B.1. Kinase Assays.

Inhibition of CDKs and other kinases was measured by radiometric assay using the Millipore KinaseProfiler services. Half-maximal inhibition ($IC_{50}$) values were calculated from 10-point dose-response curves and apparent inhibition constants (K) were calculated from the $IC_{50}$ values and appropriate $K_m$ (ATP) values for the kinases in question.

B.2. MTT Proliferation Assay.

The compounds from the examples above were subjected to a standard cellular proliferation assay using the method described previously in S. Wang et al. J Med Chem. 2004, 47, 1662-1675. The data analysis used program Deltasoft 3™ and Microsoft Excel to determine $GI_{50}$ values (concentration of test compound which inhibits cell growth by 50%).

B.3. Ex Vivo CLL Assay.

Patients' cells and clinical details. Peripheral blood samples from CLL patients and age-matched normal controls were obtained with informed consent. CLL was defined by clinical criteria as well as cellular morphology and the co-expression of CD19 and CD5 in lymphocytes simultaneously displaying restriction of light-chain rearrangement.

Primary CLL cell culture conditions. Freshly isolated peripheral blood lymphocytes ($1×10^6$/ml) were cultured in RPMI medium (Invitrogen, Paisley, UK) supplemented with 100 units/ml penicillin, 100 µg/ml streptomycin, 10% fetal calf serum and 5 ng/ml IL-4. Normal B-cells were purified by negative selection using $CD3^+$ Dyanbeads and normal T-cells were purified by negative selection using $CD19^+$ Dynabeads (Invitrogen, Paisley, UK); purity was assessed by flow cytometry and only samples with >95% target cells were used in subsequent experiments. Lymphocytes were incubated at 37° C. in a humidified 5% carbon dioxide atmosphere in the presence of compound ($1\times10^{-7}$-$1\times10^{-5}$M) for up to 48 h. In addition, control cultures were set up in which no drug was added to normal and leukaemic lymphocytes. Cells were subsequently harvested by centrifugation and were analyzed by flow cytometry using the methods outlined below. Experiments were performed either in duplicate or triplicate.

Measurement of apoptosis. Cells were harvested and labelled with CD19-Allophycocyanin (APC) (Caltag, Buckingham, UK) and then resuspended in 200 μl of binding buffer contain 4 μl of Annexin V labelled with fluorescein isothiocyanate (FITC) (Bender Medsystems, Vienna, Austria). Apoptosis was quantified in the $CD19^+$ CLL cells using an Accuri C6 flow cytometer (Becton Dickinson, CA, USA). At least 10,000 events were acquired and data was subsequently analysed using FlowJo 7.6 software (Tree Star Inc., OR, USA). $LD_{50}$ values (the concentration of drug required to kill 50% of cells) were derived from the dose-response curves.

C. Determination of Pharmacokinetics

For PK measurements male adult CD1 mice weighing 25-30 g (Charles River) are split into weight matched groups of 3 per group. The mice were held at the scruff of the neck and orally dosed via a metal gavage directly into the stomach. Immediately after dosing mice are returned to their cage, plastic box cage with sawdust bedding, and food and water available. Blood samples were collected from the mouse under anaesthesia by cardiac puncture using a 1 mL syringe and 25 gauge needle at time zero and at intervals up to 8 h. Harvested blood was centrifuged at 7000×G for 2 minutes, and the plasma aspirated and frozen at −20° C. until analysis. Quantitative compound level analysis was carried out using LC-MS/MS methods. Pharmacokinetic data derived using PK Solutions 2.0, non-compartmental analysis. Oral bioavailability (% F) was calculated by taking the ratio of dose-normalised AUC values from oral versus parenteral dosing.

Results

Biological activity of the example compounds is summarised in Table 1.

TABLE 1

| Compound | B.1. Kinase inhibition, $K_i$ nM | | | | | | | | | B.2. 48h-MTT cytotoxicity $GI_{50}$ μM | |
| --- | --- | --- | --- | --- | --- | --- | --- | --- | --- | --- | --- |
| | CDK9T1 | CDK1B | CDK2A | CDK5p35 | CDK6D3 | CDK7H | Aurora A | Aurora B | GSK3β | MCF-7 | HCT-116 |
| Comparator | 6.0 | 12 | 4 | — | 205 | 114 | — | 3 | 2 | 0.48 | 0.44 |
| Example 1 (CDKI-73) | 4.0 | 4.0 | 3.0 | 0.5 | 167 | 91.0 | 3.0 | <0.5 | 10.0 | 0.03 | 0.03 |
| Example 2 | 3.0 | 7.0 | 3.0 | 1.5 | 116 | 78 | 7.5 | 1.5 | 17 | 0.41 | 0.05 |
| Example 3 | 10.5 | 19 | 10 | 1.5 | 87.5 | 695 | — | — | — | 0.06 | 0.03 |

TABLE 2

Biological and pharmaceutical properties of the compound of Example 1 compared with the comparator compound (compound 1.9 in WO/2009/118567 A2)

| Parameters | | Comparator | Example 1 (CDKI-73) |
| --- | --- | --- | --- |
| B1 Biochemical activity, $K_i$ μM | CDK9-cyclin T1 | 0.006 | 0.004 |
| | CDK1-cyclin B | 0.012 | 0.004 |
| | CDK2-cyclin A | 0.004 | 0.003 |
| B2 48h-MTT Antiproliferative activity $GI_{50}$ μM | MCF-7 (human breast carcinoma) | 0.48 | 0.05 |
| | HCT-116 (human colon carcinoma) | 0.43 | 0.06 |
| B3 Ex vivo efficacy, $LD_{50}$ μM | Patient CLL B-cells | 0.43 | 0.08 |
| | Normal B-cells | 89 | 40.5 |
| | Normal T-cells | 350 | 506.3 |
| C Mice PK, 10 mg/kg, po | Oral bioavailability F % | 7 | 56 |

Example 6

Synergistic Combination Between the Compound of Example 1 (CDKI-73) and Fludarabine Methods Cell Isolation and Culture Peripheral blood samples from CLL patients were obtained in accordance with the ethical approval obtained from South East Wales Research Ethics Committee (02/4806). Lymphocytes were separated using Ficoll-Hypaque (Sigma, Poole, UK) and autologous plasma was collected for use in some experiments. Separated lymphocytes were maintained in RPMI medium supplemented with 10% fetal bovine serum (FBS), penicillin (50 U/ml), streptomycin (50 μg/ml) and recombinant human IL-4 (R and D Systems, Abingdon, UK) (5 ng/ml). Mouse embryonic fibroblast L-cells, either non-transfected (NTL) or L-cells expressing CD40 ligand (CD40L) [Walsby et al. (*Oncotarget* 3, 525-34 (2012)], were used where indicated as feeder layers.

Determination of Synergy Between CDK9 Inhibitors and Fludarabine

CDKI-73 was combined with fludarabine at an experimentally determined fixed molar ratio of 100:1 (fludarabine: CDKI-73=10 μM: 0.1 μM) according to the method essentially as described by Walsby et al. (*Oncotarget* 3, 525-34 (2012)). CLL cells were treated with both CDKI-73 and fludarabine alone and in combination to determine whether there were synergistic interactions between the two agents. Synergy was calculated according to the Chou and Talalay method (Chou et al., *Adv Enzyme Regul* 22, 27-55 (1984)).

Real-Time Reverse Transcription-PCR

Untreated cells and cells treated with CDKI-73, fludarabine or their combination (fludarabine: CDKI-73, 100:1) for 4 h using the method described by Walsby et al. (*Oncotarget* 3, 525-34 (2012)).

Microarray Procedures

The detailed protocol for sample preparation and microarray processing is available from Affymetrix (http://www.affymetrix.com). Briefly, total RNA was extracted from CLL cells treated with 0.1 μM CDKI-73, 10 μM fludarabine or the two drugs in combination for 4 h. First strand complementary DNA (cDNA) was synthesized from 5 μg total RNA using a T7-(dT)24 primer (Genset Corp, San Diego, Calif., USA) and reverse-transcribed with the Superscript Double-Stranded cDNA Synthesis Kit (Invitrogen Life Technologies, San Diego, Calif., USA). After second strand synthesis, the resulting cDNA was subjected to an in vitro transcription reaction using a Bioarray kit (Enzo Diagnostics, New York, N.Y., USA) to generate biotinylated cRNA. This was subsequently fragmented and hybridized to the Affymetrix U133 2.0 Gene Chips. After hybridization, each microarray was washed, stained and scanned with an argon-ion confocal laser, with excitation at 488 nm and detection at 570 nm.

Statistical Analysis

The significance of differences between experimental conditions was determined using the Student's t test for paired and unpaired observations. To assess the interaction between agents, the median effect method was employed using CalcuSyn software (CalcuSyn; Biosoft International, Ferguson, Mo.). The combination index was calculated for the two-drug combination using an experimentally determined fixed concentration ratio. Combination index values <1.0 indicated a synergistic interaction. Affymetrix gene expression data were processed using Partek Genomics Suite (Partek Inc. Saint Louis, USA).

Results

Figure Legend

FIG. 1. CDKI-73 Synergizes with Fludarabine Even on Pro-Survival CD40L Co-Culture FIG. 1(A)—shows the effect of different molar ratios of fludarabine:CDKI-73 on primary CLL cells in 48 h cytotoxicity assays. The combination ratios were based on the $LD_{50}$ values for each drug and the maximum tolerated dose of fludarabine in viva A ratio of 100:1 was shown to give the strongest synergy in all the samples tested.

CDKI-73 Synergizes with Fludarabine

Figure 1A:
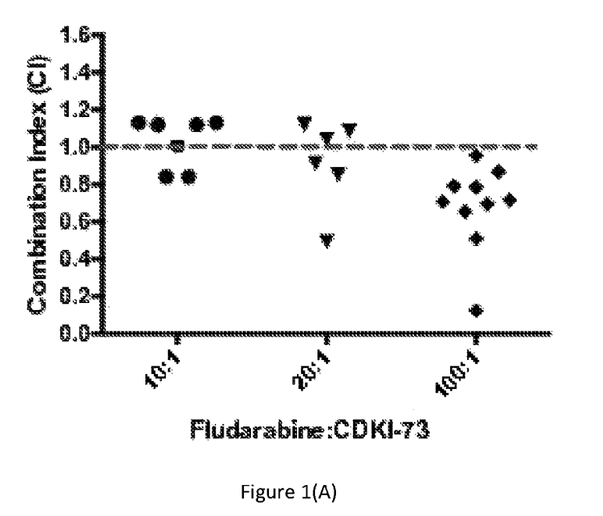
Figure 1B:
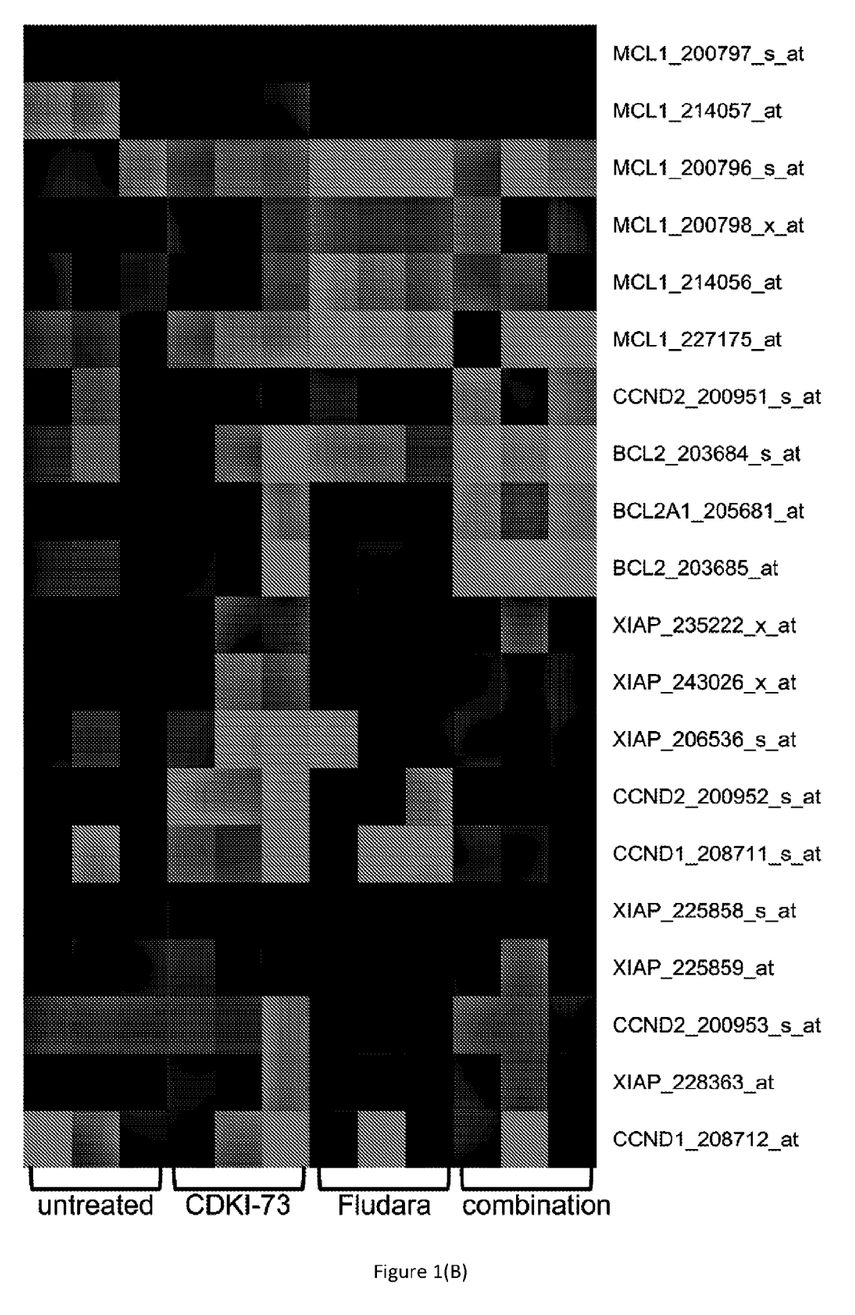
FIG. 1(B)—shows gene expression profiling revealed a potential mechanism for the synergy observed. CDKI-73 inhibited the transcription of MCL1, BCL2, XIAP and CCND1 and D2. In contrast, fludarabine induced MCL1, BCL2 and XIAP transcription providing a rationale for the drug resistance that commonly occurs following retreatment with fludarabine. Importantly, the combination of CDKI-73 and fludarabine showed a marked repression of MCL1, BCL2, XIAP and CCND1 and D2.

Fludarabine-based treatment options are currently the standard of care for CLL patients without significant comorbidities. In this experiment, the in vitro effects of combining CDKI-73 with fludarabine were assessed. The fixed molar ratio used in this study was determined experimentally. The ratios tested were constrained by the maximum clinically achievable dose of fludarabine and the relative potency of each agent. The most synergistic interaction was achieved using a fixed molar ratio of 100:1 (fludarabine:CDKI-73) (FIG. 1A). All of the samples tested (n=10) showed synergy, with a median combination index of 0.71. In an attempt to understand the underlying molecular mechanisms for the synergy observed, gene expression profiling of CLL cells treated with 10 μM fludarabine, 0.1 μM CDKI-73 and the combination of the two agents (100:1) was performed. Gene expression changes were observed under all drug treatment conditions when compared with untreated controls. FIG. 1B shows the relative expression changes in genes known to be susceptible to RNA polymerase II inhibition. CDKI-73 as a single agent down regulated MCL1, BCL2, XIAP and CCND1 and CCND2. In contrast, fludarabine induced the expression of MCL1 but this induction was reversed by the combination of CDKI-73 and fludarabine. Clearly other molecular mechanisms may also contribute to the synergy observed between these agents but the suppression of MCL1, BCL2, XIAP and CCND1 and CCND2 seem likely to be major factors.

Figure 1C:
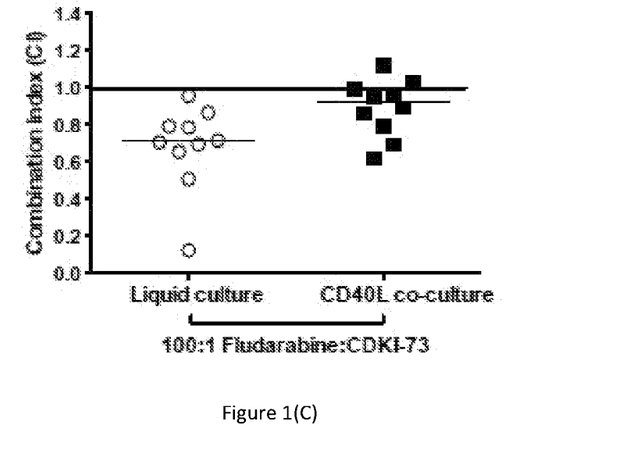
FIG. 1(C)—shows the effect of the combination under pro-survival, CD40L-expressing co-culture conditions. These conditions are known to induce marked resistance to fludarabine but synergy was retained when used in combination with CDKI-73.
Figure 1D:
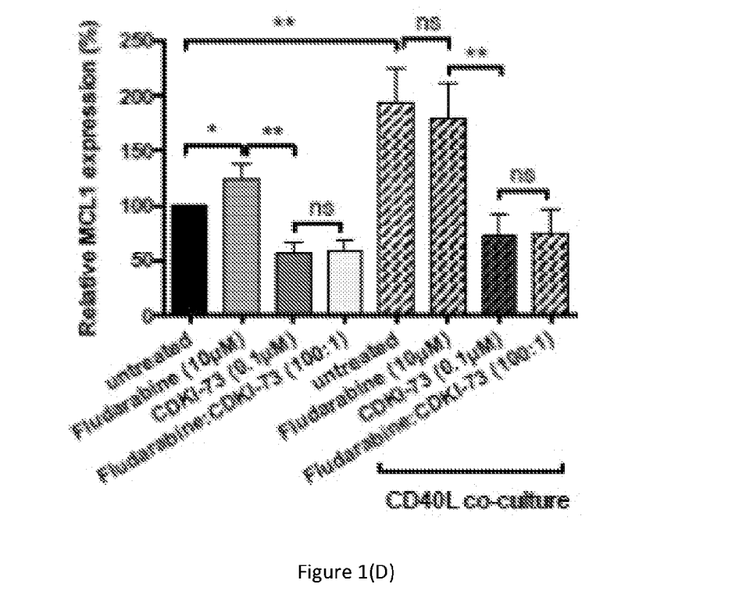
FIG. 1(D)—shows the relative expression of MCL1 under the various drug conditions with and without co-culture with CD40L-expressing mouse fibroblasts (assessed using QRT-PCR). In keeping with the gene expression profiling data, CDKI-73 repressed MCL1 both alone and in combination with fludarabine under all conditions. In contrast fludarabine induced MCL1, which was maintained under co-culture conditions.

CDKI-73 Remains Synergistic with Fludarabine Under Pro-Survival Co-Culture Conditions It has been shown previously that co-culture of primary CLL cells with CD40L-expressing mouse embryonic fibroblasts completely abrogates the cytotoxic effects of fludarabine (Walsby et al. *Oncotarget* 3, 525-34 (2012)). In the experiment, we investigated whether the addition of CDKI-73 could reverse the drug resistance to fludarabine observed under these conditions. Although the combination index increased (median=0.92), 8/10 samples tested showed cytotoxic synergy and the other two additive effects under these pro-survival culture conditions (FIG. 1C). Analysis of the changes in transcription of MCL1 under these conditions confirmed that co-culture significantly induced MCL1 both in untreated CLL cells and cells exposed to fludarabine. In contrast, CDKI-73 significantly inhibited MCL1 transcription as a single agent and in combination with fludarabine (FIG. 1D).

What is claimed is:
1. A compound of formula I shown below:

wherein:
$R_1$ is $NH_2$ or NHMe;
$R_2$ is halo; and
one of $R_3$ or $R_4$ is hydrogen and the other is selected from —$SO_2NH_2$, —$SO_2NHMe$, —$SO_2NMe_2$, —$SO_2NHEt$, or —$SO2NEt_2$;
or a pharmaceutically acceptable salt thereof.

2. A compound according to claim 1, wherein $R_1$ is NHMe.

3. A compound according to claim 1, wherein $R_2$ is fluoro or chloro.

4. A compound according to claim 1, wherein one of $R_3$ or $R_4$ is hydrogen and the other is —$SO_2NH_2$.

5. A compound according to claim 4, wherein $R_3$ is hydrogen and $R_4$ is selected from —$SO_2NH_2$, —$SO_2NHMe$ or —$SO_2NMe_2$.

6. A compound according to claim 5, wherein $R_3$ is hydrogen and $R_4$ is —$SO_2NH_2$.

7. A compound according to claim 1, which is selected from any one of the following:

3-(5-fluoro-4-(4-methyl-2-(methylamino)thiazol-5-yl)pyrimidin-2-ylamino)benzene sulfonamide;

3-(5-fluoro-4-(4-methyl-2-aminothiazol-5-yl)pyrimidin-2-ylamino)benzene sulfonamide;

3-(5-chloro-4-(4-methyl-2-(methylamino)thiazol-5-yl)pyrimidin-2-ylamino)benzene sulfonamide;

or a pharmaceutically acceptable salt thereof.

8. A pharmaceutical composition comprising a compound according to claim 1, or a pharmaceutically acceptable salt thereof, in admixture with a pharmaceutically acceptable diluent or carrier.

9. A method of treating chronic lymphocytic leukaemia (CLL) in a patient in need of such treatment, said method comprising administering to said patient a therapeutically effective amount of a compound according to claim 1, or a pharmaceutically acceptable salt thereof.

10. A method of synthesizing a compound of the formula I according to claim 1, the method comprising:
a) reacting a compound of formula A:

wherein $R_1$ and $R_2$ each have any one of the meanings set out hereinbefore;
with a compound of formula B:

wherein $R_3$ and $R_4$ have any one of the meanings set out hereinbefore; and
b) optionally thereafter, and if necessary:
i) removing any protecting groups present;
ii) converting the compound formula I into another compound of formula I; and/or
iii) forming a pharmaceutically acceptable salt thereof.

* * * * *